US008969256B2

(12) United States Patent
Takayama et al.

(10) Patent No.: US 8,969,256 B2
(45) Date of Patent: Mar. 3, 2015

(54) SOLUTION MICROARRAYS AND USES THEREOF

(75) Inventors: Shuichi Takayama, Ann Arbor, MI (US); Arlyne Simon, Ann Arbor, MI (US); Nien-Tsu Huang, Ann Arbor, MI (US); Katsuo Kurabayashi, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 23 days.

(21) Appl. No.: 13/825,721

(22) PCT Filed: Sep. 22, 2011

(86) PCT No.: PCT/US2011/052772
§ 371 (c)(1),
(2), (4) Date: May 17, 2013

(87) PCT Pub. No.: WO2012/040473
PCT Pub. Date: Mar. 29, 2012

(65) Prior Publication Data
US 2013/0225438 A1    Aug. 29, 2013

Related U.S. Application Data

(60) Provisional application No. 61/386,258, filed on Sep. 24, 2010.

(51) Int. Cl.
*G01N 33/536* (2006.01)
*G01N 33/53* (2006.01)
(Continued)

(52) U.S. Cl.
CPC ........ *G01N 33/536* (2013.01); *G01N 33/54313* (2013.01); *G01N 33/54393* (2013.01); *G01N 33/6845* (2013.01)

USPC ................. 506/9; 506/18; 435/7.1; 435/7.92; 436/501

(58) Field of Classification Search
CPC . G01N 33/536; G01N 33/53; G01N 33/5306; G01N 33/543; G01N 33/54393; G01N 33/6845; G01N 33/6854; C40B 30/04; C40B 40/10
USPC .................. 435/7.1, 7.92; 436/501; 506/9, 18
See application file for complete search history.

(56) References Cited

U.S. PATENT DOCUMENTS 4,672,024 A * 6/1987 Giaever et al. ................ 430/396
6,048,715 A   4/2000 Haynes et al.
(Continued)

FOREIGN PATENT DOCUMENTS

EP        709679 B1    7/1999
WO     96/38577 A1   12/1996
(Continued)

OTHER PUBLICATIONS

Glokler et al., "Protein and antibody microarray technology", Journal of Chromatography B 2003, 797:229-240.*
(Continued)

*Primary Examiner* — Samuel Woolwine
*Assistant Examiner* — Kaijiang Zhang
(74) *Attorney, Agent, or Firm* — Tanya A. Arenson; Casimir Jones, S.C.

(57) ABSTRACT

The present invention relates to solution microarrays. In particular, the present invention relates to an aqueous 2-phase system for solution microarrays and uses thereof. The present invention further relates to systems and methods for performing assays within the solution microarrays (e.g., diagnostic assays).

16 Claims, 8 Drawing Sheets

(51) Int. Cl.
*C40B 30/04* (2006.01)
*C40B 40/10* (2006.01)
*G01N 33/543* (2006.01)
*G01N 33/68* (2006.01)

(56) References Cited

U.S. PATENT DOCUMENTS

2006/0078908 A1 4/2006 Pitner et al.
2009/0209735 A1 8/2009 Koo et al.

FOREIGN PATENT DOCUMENTS

| WO | 00/40598 A1 | 7/2000 |
| WO | 2010/027590 A2 | 3/2010 |
| WO | WO 2010027590 A2 * | 3/2010 |

OTHER PUBLICATIONS

Templin et al., "Protein Microarrays and Multiplexed Sandwich Immunoassays: What Beats the Beads?" Combinatorial Chemistry & High Throughput Screening 2004, 7:223-229.*

* cited by examiner

SOLUTION MICROARRAYS AND USES THEREOF

CROSS-REFERENCE TO RELATED APPLICATIONS

This present application is a national phase application under 35 U.S.C. §371 of PCT International Application No. PCT/US2010/060278, filed Sep. 22, 2011, which claims priority to U.S. Provisional Patent Application 61/386,258, filed Sep. 24, 2010, each of which are herein incorporated by reference in its entirety.

FIELD OF THE INVENTION

The present invention relates to solution microarrays. In particular, the present invention relates to an aqueous 2-phase system for solution microarrays and uses thereof. The present invention further relates to systems and methods for performing assays within the solution microarrays (e.g., diagnostic assays).

BACKGROUND OF THE INVENTION

The fields of life science research and pharmaceutical development are dependent upon highly selective and sensitive quantitative assays for a wide range of different biomolecules (such as proteins, antibodies, cytokines, receptors, enzymes, peptides, nucleic acids, hormones, and the like) in complex clinical or biological samples (such as blood, urine, tissue or cellular extracts, cell culture supernatants, bioprocess feedstreams, and the like). In typical samples (which may contain thousands of different molecular species) the analytes of interest may be present at extremely low concentrations (nanograms per milliliter or less), but the samples may be available only in very small quantities (microliters or less). The rapid growth in the field of biotechnology and the introduction of many potential new drug targets from genomic research have created an increasing demand for more rapid and efficient analytical methods, without any sacrifice in performance.

In order to simultaneously obtain high selectivity (the ability to measure one very specific molecule in a complex mixture) and high sensitivity (the ability to accurately quantify very small concentrations or amounts), a number of analytical methods have been developed which couple powerful molecular separations with extremely responsive detection methods.

Existing methods, such as ELISA assays suffer from insufficient sensitivity and specificity and are expensive. New methods are needed for diagnostic assays to allow for sensitive and specific detection of analytes.

SUMMARY OF THE INVENTION

The present invention relates to solution microarrays. In particular, the present invention relates to an aqueous 2-phase system for solution microarrays and uses thereof. The present invention further relates to systems and methods for performing assays within the solution microarrays (e.g., diagnostic assays).

Embodiments of the present invention provide kits, systems, apparatuses, and methods for use in performing assays within multiphase solution microarrays. Embodiments of the present invention provide assays with improved sensitivity relative to traditional assays.

For example, in some embodiments, the present invention provides a system, comprising: a) a first solution comprising a first polymer and reagents for detecting the presence or absence of an analyte in a test sample; b) a second solution comprising a second polymer and the test sample, wherein the second solution has a different density (e.g., more or less dense) than the first solution, and wherein the first and second solutions form an aqueous two-phase system when mixed; and c) a solid or semi-solid support. In some embodiments, the first and second polymers are each one of, for example, polyethylene glycol (PEG), polyvinyl alcohol (PVA), hydroxypropyl dextran (HPD) or dextran (DEX) (e.g., DEX T10, PEG 35,000, DEX T40, PVA 105,000, HPD 500 or DEX T500). In some embodiments, the first or second solutions comprise two or more polymers (e.g., DEX-methylcellulose, DEX-polyvinyl alcohol, PEG-DEX sulfate, polyvinyl alcohol-DEX sulfate, hydroxypropyldextran-DEX or DEX sulfate-methylcellulose). In some embodiments, the reagents comprise an antibody that specifically binds to the analyte (e.g., an antigen). In some embodiments, the antibody is bound to a particle (e.g., a molecular beacon or a bead, optionally coated with dextran). In some embodiments, the reagents further comprise reagents for detecting the presence of binding of the antibody to the antigen. In some embodiments, the test sample is a nucleic acid and the reagents provide reagents for detection of the nucleic acid. In some embodiments, the aqueous two phase system has a viscosity of greater than or equal to 10 cP or less than or equal to 10 cP. In some embodiments, the system further comprises a detection component (e.g., a apparatus for detecting laser induced luminescence, fluorescence resonance energy transfer, fluorescence polarization, transmittance, and color change).

The present invention further provides a method, comprising: a) contacting a solid or semi-solid support with a first solution comprising a first polymer and reagents for detecting the presence or absence of an analyte in a test sample to form a coated support; b) contacting a portion of the coated support with a second solution comprising a second polymer and a test sample, wherein the first and second solutions form an aqueous two-phase system when mixed; and c) detecting the presence or absence of the analyte in the test sample using the reagents. In some embodiments, the first and second solutions are not pre-equilibrated prior to performing the assay. In some embodiments, detecting the presence or absence of the analyte in the test sample comprises the use of a detection method (e.g., laser induced luminescence, fluorescence resonance energy transfer, fluorescence polarization, transmittance, or color change). In some embodiments, the method is a singleplex or multiplex assay (e.g., immunoassay).

Additional embodiments are described herein.

DEFINITIONS

Figure 1:
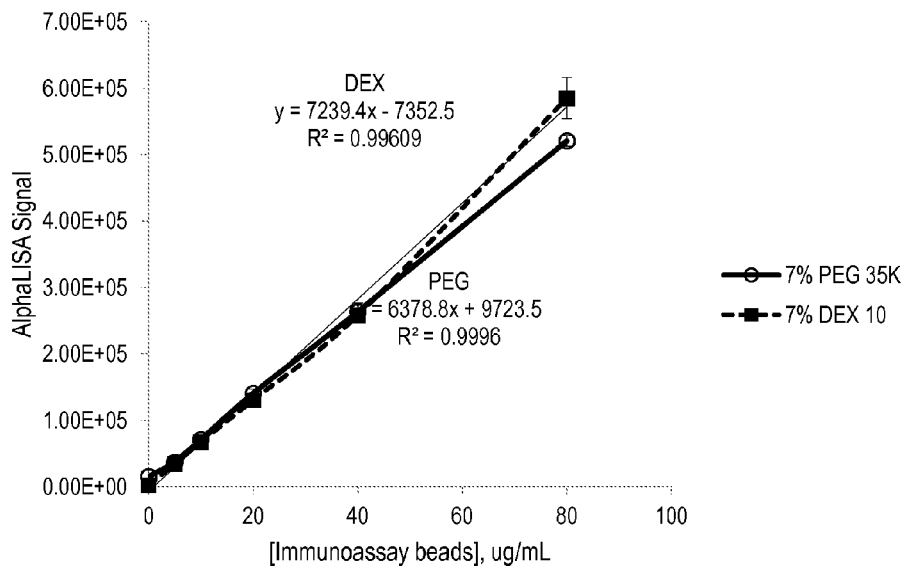
FIG. 1 shows the correlation between fluorescent signal and concentration of dextran-coated immunoassay beads in PEG and DEX polymer solutions.

To facilitate an understanding of the present invention, a number of terms and phrases are defined below:

The term "assay reagents" as used herein is used in the broadest sense and may refer to freely-circulating antibody-conjugated beads, surface-tethered antibodies, nucleic acid reagents, or other biomolecules.

The term "pre-equilibrated" as used herein is used in the broadest sense to refers to a two-phase system prepared such that polymer solutions are equilibrated (e.g., by composition) towards their thermodynamically most stable states prior to their intended application (e.g., immunoassay).

The term "non pre-equilibrated" as used herein is used in the broadest sense to refer to individually prepared polymer solutions that comprise an aqueous two-phase system significantly different from their thermodynamically most stable state. In some embodiments, when phases are non pre-equilibrated, the two phases of the ATPS become equilibrated within the assay system during the assay via convection and diffusion enhancing mass transport.

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "viscosity" refers to a measure of the resistance of a fluid deformed by either shear stress or tensile stress. In some embodiments, viscosity is measured in poise or centipoise (cP) units.

DETAILED DESCRIPTION OF THE INVENTION

The present invention relates to solution microarrays. In particular, the present invention relates to an aqueous 2-phase system for solution microarrays and uses thereof. The present invention further relates to systems and methods for performing assays within the solution microarrays (e.g., diagnostic assays).

The compositions and methods of embodiments of the present invention provide the unique features of the use aqueous two-phase systems for the confinement of both multiple assay reagents (e.g., antigens and capture and detection antibodies) in nanoliter to microliter volumes of assay droplets. Certain aspects of the invention are illustrated using immunoassays, although the solution microarrays are suitable for use in a variety of assays.

I. Microarrays

In some embodiments, the present invention provides multi (e.g., 2) phase solution based microarrays and uses thereof. The present invention is not limited to particular components of the microarray. In some embodiments, the components are aqueous polymers. Preferred polymers are those that form an aqueous two phase system (ATPS) at a wide range of temperatures. Examples of suitable polymers include, but are not limited to, polyethylene glycol (PEG), polyvinyl alcohol (PVA), hydroxypropyl dextran (HPD) or dextran (DEX), and combinations of other polymers such as DEX-methylcellulose, DEX-polyvinyl alcohol, PEG-DEX sulfate, polyvinyl alcohol-DEX sulfate, hydroxypropyldextran-DEX, and DEX sulfate-methylcellulose. Other specific, non limiting examples include but are not limited to, DEX T10, PEG 35,000, DEX T40, PVA 105,000, HPD 500 and DEX T500. In some embodiments, DEX polymers are used in concentrations above 1% to suppress background noise and enhance sensitivity.

In some embodiments, charged polymers like diethylaminoethyl (DEAE) dextran or carboxymethyldextran are mixed with the DEX phase to promote charged analytes (e.g., cytokines) partitioning or localizing to the DEX phase.

In other embodiments, ATPS that exhibit variable phase separation with temperature are utilized. In some embodiments, such systems utilize low or high molecular weight polymers.

In some embodiments, a first solution comprising a first polymer and detection reagents for detection of an analyte of interest or a test sample (e.g., comprising the analyte of interest) is dispensed onto a solid support. In some embodiments, a second solution comprising a second polymer detection reagents for detection of an analyte of interest or a test sample (e.g., comprising the analyte of interest) is dispensed onto the first solution, thus forming an aqueous two phase system. In some embodiments, a transport component (e.g., an array of slot pins) is then used to transfer the second solution onto the array comprising the first solution. For example, in some embodiments, a multiplex dispenser that allows different materials to be added to different spots on the array is utilized. In some embodiments, the dispenser is a plurality of pins or other dispensing components affixed to a single transport component. In some embodiments, the transport component is automated.

In some embodiments, aqueous two phase polymer formulations that give relatively less viscous phases (e.g., less than 10 cP) that enable reagents to diffuse more freely and enhance detection sensitivity are used. Examples, include, but are not limited to DEX T10 that is less viscous than an ATPS with higher molecular weight DEX but also is stable and not precipitating like DEX T3.5.

In some embodiments, aqueous two phase systems with relatively high viscosity (e.g., more than 10 cP) that provide higher stability in terms of response to convection due to higher viscosity are utilized. Examples include, but are not limited to, an ATPS with DEX T40 that gives a higher viscosity ATPS.

In some embodiments, detection reagents (e.g., antibodies) are bound to a particle or are in a suspension. Examples include, but are not limited to, dextran-coated microspheres, a proximity bead assay reagent or a molecular beacon reagent.

In some embodiments, the two-phase system is prepared such that polymer solutions are equilibrated (e.g., by composition) towards their thermodynamically most stable states prior to their intended application (e.g., assay). In other embodiments, individually prepared polymer solutions comprise an aqueous two-phase system significantly different from their thermodynamically most stable state (e.g., non-equilibrated). In some embodiments, when phases are non pre-equilibrated, the two phases of the ATPS become equilibrated within the assay system during the assay via convection and diffusion enhancing mass transport.

II. Uses

The solution based microarrays of the present invention find use in a variety of applications. In some embodiments, the arrays are utilized in performing assays (e.g., diagnostic, drug screening, or research assays).

In some embodiments, the first solution comprises a first polymer and a reagent for detection of an analyte and the second solution comprises a second polymer and the test sample suspected of containing the analyte. In other embodiments, the first solution comprises a first polymer and a test sample suspected of containing the analyte and the second solution comprises a second polymer and reagents for detecting the analyte. In some embodiments, the first solution is applied to a solid surface. The second solution is then selectively applied on top of the first solution, forming 2-phase solution arrays. Interaction of the reagent specific for the analyte and the analyte is then detected using any suitable method.

The present invention is not limited to a particular analyte. Exemplary analytes include, but are not limited to, antigens, antibodies, nucleic acids, proteins (e.g., biologically relevant proteins), small molecules, hormones, receptors, ligands and the like. For example, in some embodiments, assays detect cytokines or biomarkers such as $TNF\alpha$, IL-8, IL-6, IL-2R$\alpha$, and elafin.

In some embodiments, the analyte sample is an antigen-containing buffer solution, animal or human blood plasma or serum specimen, or animal or human saliva.

The present invention is not limited to a particular detection reagent. Any detection reagent that specifically interacts (e.g., binds) to an analyte of interest and partitions selectively to one of the two aqueous phases is suitable. Exemplary detection reagents include, but are not limited to, antibodies, receptors, ligands and the like.

Embodiments of the present invention are illustrated with immunoassays. However, the present invention is not limited to immunoassays. One skilled in the art recognizes that the systems and methods described herein are applicable to any number of biological or other assays.

For example, in some embodiments, antigen samples are mixed with a second polymer and diffuse along a concentration gradient into droplets of the first polymer on a solid support to form an aqueous 2-phase system. Once in the 2-phase system, antigens are sandwiched between the capture and detection antibodies and a signal (e.g., fluorescent or laser induced luminescence signal) is emitted. This immunoassay (or other assay) reagent confinement is advantageous to biomarker assays because it enables the use of less reagents and a reduction in assay costs. In some embodiments, the solution microarray is used to simultaneously analyze concentrations of multiple biomarkers in sample specimens (e.g., multiplex assays). Spatial localization of antibody or other reagents, inhibits cross-reactivity that typically occurs in multiplex assays.

Interaction of an analyte and a detection reagent specific for the analyte are detected using any suitable method. In some embodiments, additional reagents are utilized in diagnostic assays (e.g., reporter molecules, chemical detection reagents, fluorescent reagents and the like).

In some embodiment, a detection apparatus (e.g., a fluorometer, spectrometer, camera, etc.) is utilized in the detection of an interaction between the analyte and the detection reagent. In some embodiments, the detection apparatus described herein (e.g., in FIG. 6) is utilized. In some embodiments, detection methods include, but are not limited to laser induced luminescence, FRET (fluorescence resonance energy transfer), fluorescence polarization, transmittance, fluorescence anisotropy, raman spectroscopy or color change. In some embodiments, the optical setup includes a laser diode for reagent excitation and a CCD or PMT camera for emission signal detection.

In some embodiments, assays and read out is performed in a high throughput manner. In some embodiments, high throughput methods are automated. In some embodiments, multiplex assays are performed for the simultaneous detection of multiple analytes.

The present invention further provides systems and kits comprising the solution arrays described herein. In some embodiments, systems and kits comprise multiple solutions for forming arrays, reagents (e.g., antibodies and/or antigens), transport components (e.g., robotics), and components for read out of signal from assay results, including analysis software. In some embodiments, kits further comprise additional component useful, necessary, or sufficient for performing and analyzing the results of the methods described herein (e.g., including, but not limited to, buffers, control antigens, control antibodies, etc.).

EXPERIMENTAL

The following examples are provided in order to demonstrate and further illustrate certain preferred embodiments and aspects of the present invention and are not to be construed as limiting the scope thereof.

Example 1

This example describes the use of aqueous multiphase systems for use in performing assays (e.g., diagnostic assays). Solution Microarray for Singleplexed Cytokine Detection To show the stable partitioning of immunoassay reagents in the DEX phase of an aqueous two-phase system (ATPS), calibration curves of reagent concentration versus fluorescent signal for separate PEG and DEX phases were generated (FIG. 1). Next, a known concentration of bead-based reagents was spiked into an ATPS. After separating the PEG and DEX phases, the fluorescent signal of the PEG and DEX phases was analyzed. The partition coefficient, defined as the ration between the concentration of reagent in the PEG phase and the DEX phase, was computed as <<0.03. This value highlights that assay reagents are confined within the dextran phase.

Figure 8:
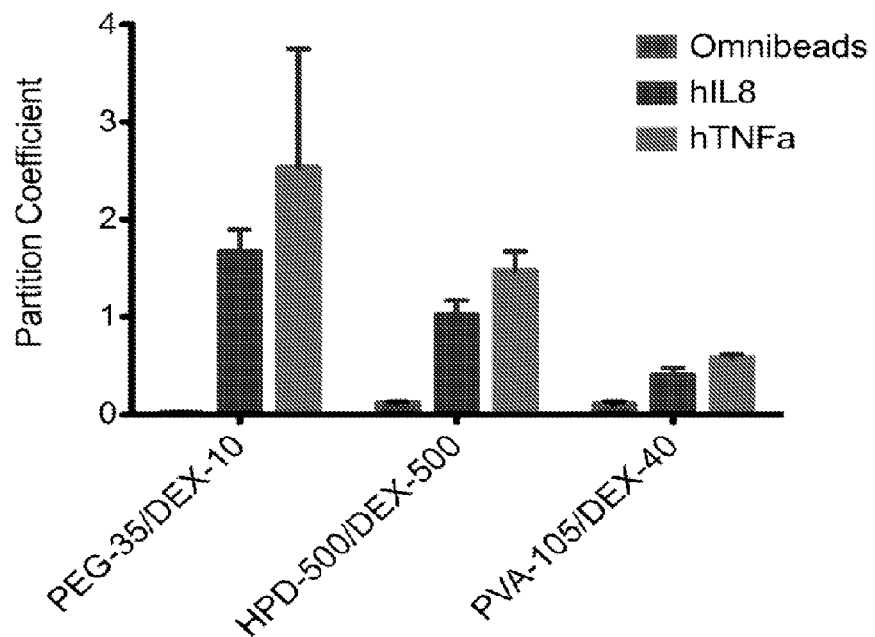
FIG. 8 shows the correlation between the partitioning/localization of AlphaLISA beads and cytokines in selected aqueous multiphase systems.

To select the optimum aqueous two-phase system (ATPS) that enabled the most stable partitioning of immunoassay reagents in the DEX phase, the partition coefficients of TNFα, IL-8, and AlphaLISA beads in the PEG/DEX, PVA/DEX, and HPD/DEX two-phase systems were calculated (FIG. 8). A known concentration of bead-based reagents was spiked into an ATPS. Carefully separating the top and bottom phases, the fluorescent signal of the PEG or PVA or HPD and DEX phases was analyzed. The partition coefficient, defined as the ratio between the concentration of reagent in the top phase and the bottom phase was computed and values highlight that all assay reagents are confined within the dextran phase in the PVA/DEX system.

Figure 2:
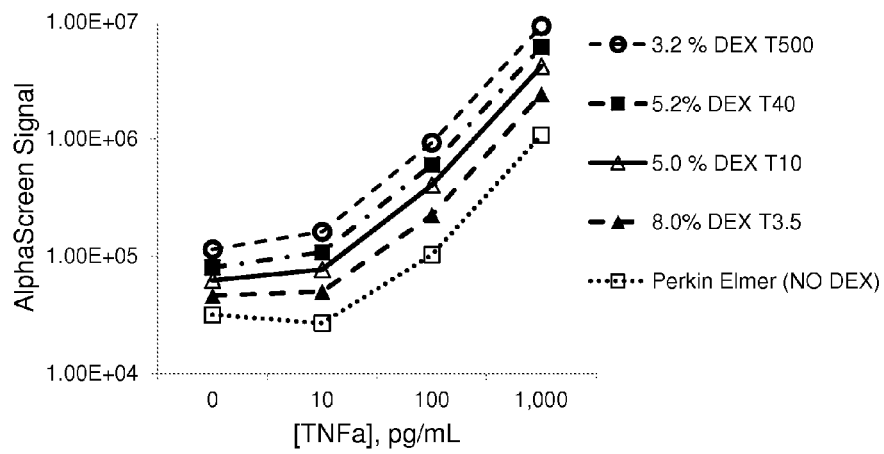
FIG. 2 shows the effect of dextran molecular weight on fluorescent assay signal in TNFα proximity-bead based AlphaLISA assays.

In these experiments, dextran with a molecular weight range from 3,500 to 500,000 Da was utilized. Different dextrans are used in other applications. To screen the effect of dextran on fluorescent signal, singleplex TNFα assays were performed in four dextrans of differing molecular weights. Specifically, the following dextrans were used: 3,500; 10,000; 40,000; and 500,000 Da. With the decrease in dextran molecular weight, a higher signal-to-noise ratio was observed (FIG. 2). Further, with the decrease in dextran molecular weight, polymer solutions were less viscous (Table I). Despite storage at 4° C., solutions that comprised of dextran 3,500 Da displayed relatively short shelf lives; dextran precipitated out of the buffer solutions after about ten days. For singleplexed and multiplexed assays, DEX T10 and DEXT40 were utilized because they have low background signals and are less viscous, allowing antigens to diffuse easily through assay droplets and thus conjugate to DEX-confined immunoassay reagents.

Figure 9:
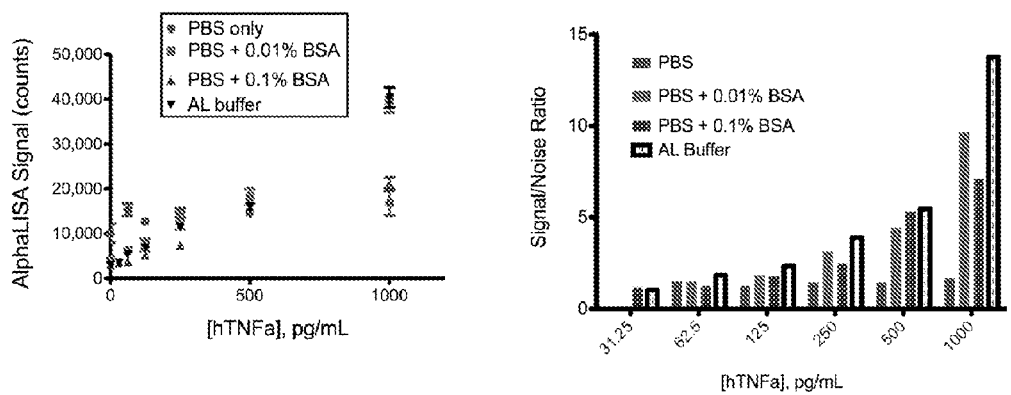
FIG. 9 shows the effect of buffers on luminescent assay signal in TNFα proximity bead-based AlphaLISA assays. Four buffers were compared: phosphate buffer saline (PBS), PBS+0.01% Bovine Serum Albumin (BSA), PBS+0.1% BSA and AlphaLISA (AL) Buffer. The latter AL Buffer constituted of 25 mM HEPES, pH 7.4, 0.1% Casein, 0.5% Triton X-100, 1 mg/mL DEX T500, and 0.05% Proclin-300.

Of the four buffers compared, phosphate buffer saline (PBS)+0.1% bovine serum albumin (BSA) was identified as the best choice for the singleplex cytokine assays because it provided the lowest detection limit, namely 9.6 pg/mL (FIG. 9).

Figure 3:
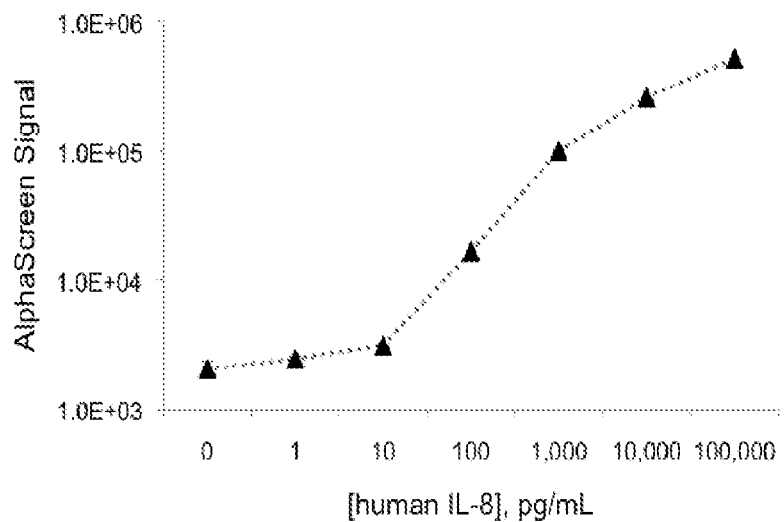
FIG. 3 demonstrates the ability of DEX T10 to enhance the sensitivity of IL-8 AlphaLISA assays.

To study the effect of dextran on fluorescent signal, 5 µL of IL-8 sample dilutions was added to 45 µL DEX T10. The DEX polymer solution contained anti-IL-8 antibody-conjugated beads. After 3 hour incubation at room temperature, assay signal was read via plate reader (FIG. 3). A dynamic range of 2.17-100,000 pg/mL IL-8 was computed. This data shows that by adding dextran, one achieves one log more of sensitivity than commercial singleplex AlphaLISA assays (1.1-30,000 pg/mL) and 2.5 logs more than commercial singleplex ELISA assays (7.5 pg/mL-2,000 pg/mL).

Figure 5:
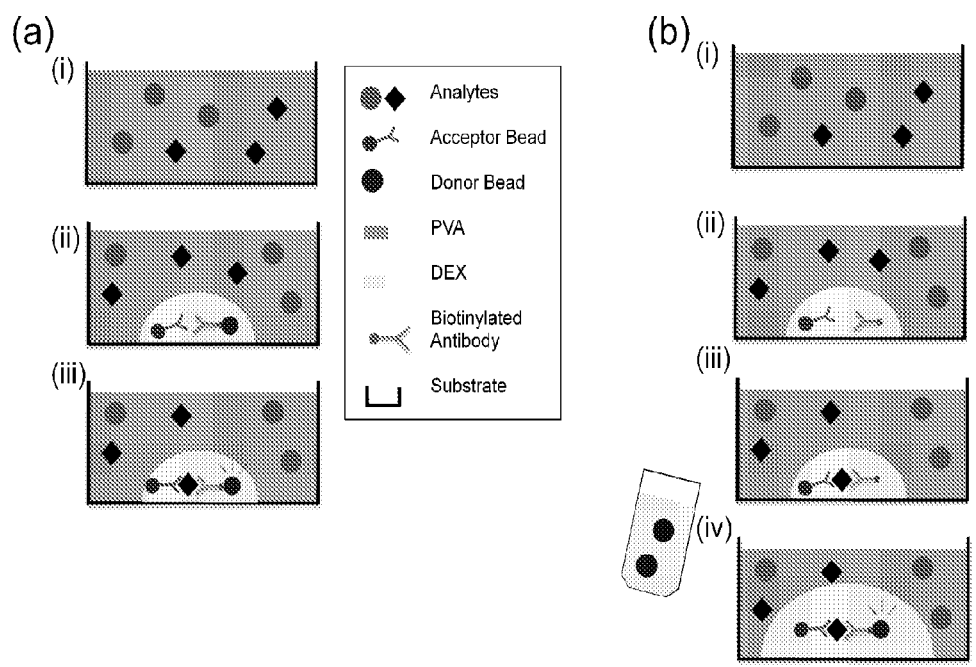
FIG. 5 shows a schematic of solution microarray technology for singleplex cytokine detection. (a) Antigen samples are mixed with PEG or PVA in wells of a microwell plate. (b) 600 nL DEX assay droplets, containing immunoassay reagents, are dispensed into the PEG or PVA solution. (c) Antigen samples diffuse freely from the PEG or PVA phase into the DEX droplets, eliciting a fluorescent signal.

FIG. 5 shows protocol when singleplex assays are conducted on microwell plates or glass substrates. In this method, antigen-containing samples are mixed with PVA and DEX assay droplets are dispensed unto glass substrates, reducing background levels and enhancing signal-to-noise ratio of the assay.

Figure 4:
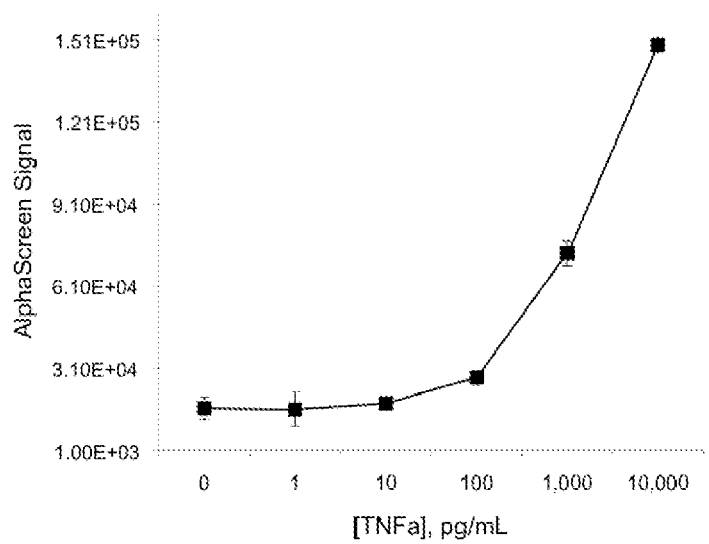
FIG. 4 shows that solution microarray enables singleplex assays in 600 mL DEX droplets.
Figure 10:
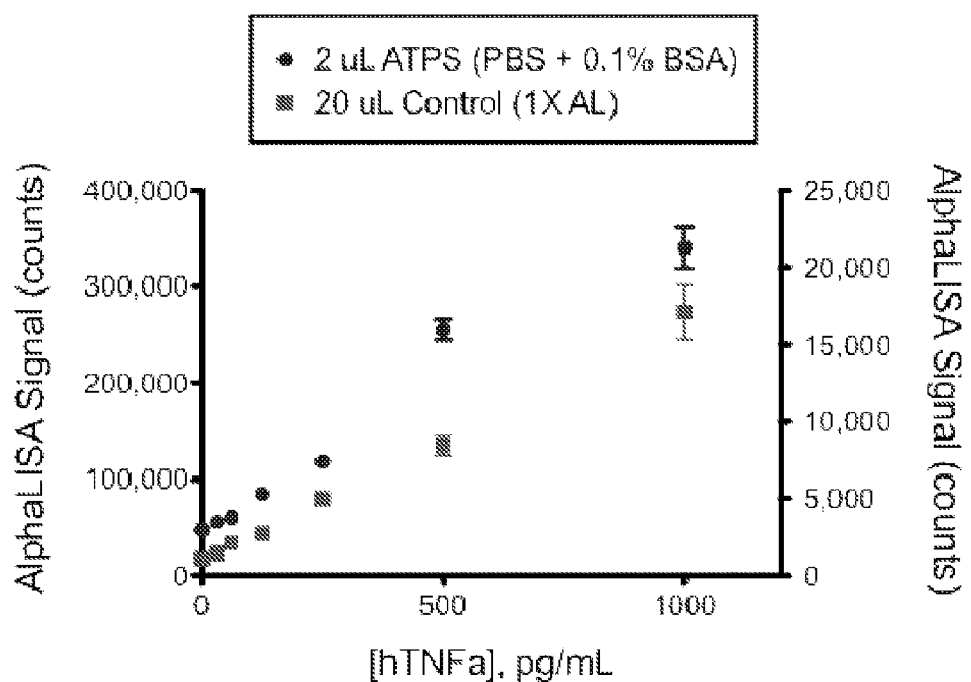
FIG. 10 shows that solution microarray technology enables singleplex assays in 2 uL DEX (not pre-equilibrated with PVA) droplets.

It was found that singleplex biomarker assays can also be performed in 0.5-2 µL DEX volumes, where assay reagents are partitioned within the DEX phase and antigens in PEG diffuse freely from the PEG into DEX assay droplets (FIGS. 4 and 10). To demonstrate this, 5 µL human TNFα was added to 20 µL PEG phase directly into wells of a microplate. 600 nL or 2 µL dextran droplets (Mw. 10,000 or 40,000), containing anti-TNFα antibody-conjugated beads were dispensed into the PEG. Solutions were incubated for 3 hours at room temperature and fluorescent signal detected via plate reader. A dynamic range of 12 pg/mL-10,000 pg/mL was achieved (FIG. 10).

Figure 6:
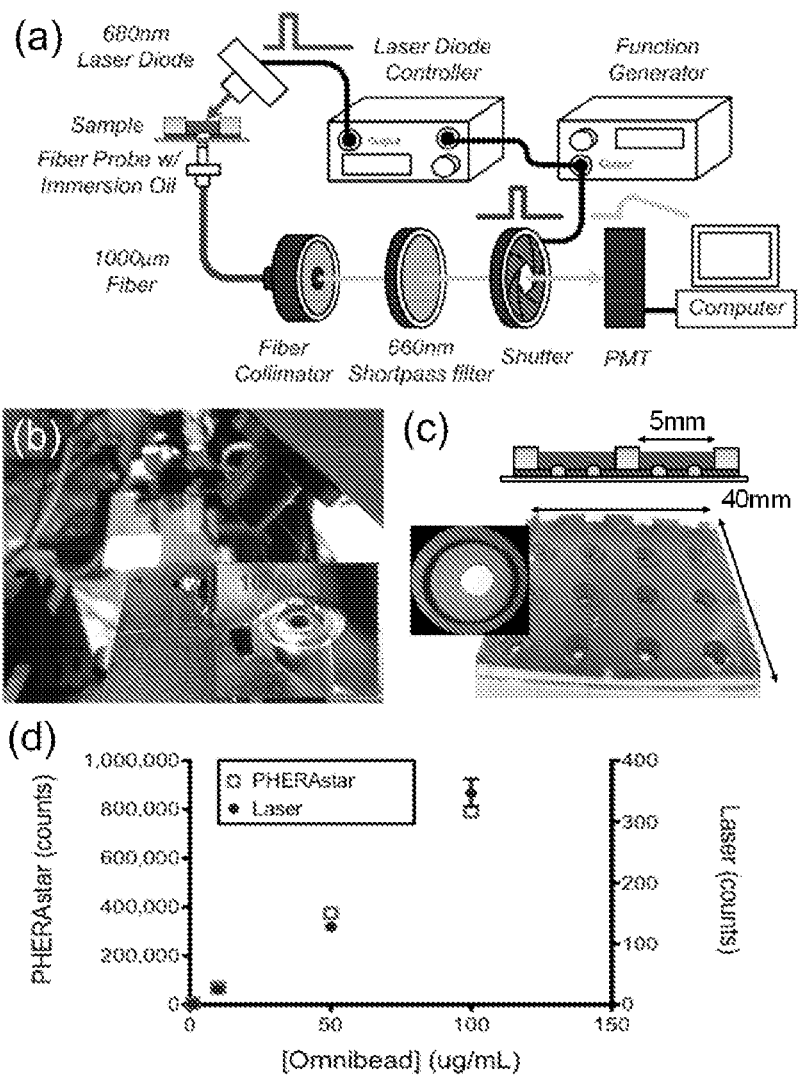
FIG. 6 shows a customized optical setup capable of measuring the luminescent AlphaLISA assay signal. (a) Schematic of customized optical setup, containing a laser diode to excite assay reagents at 680 nm and a CCD or PMT camera for emission signal detection at 615 nm. (b) Image of fiber probe, positioned directly beneath sample for optimum assay signal detection. (c) Poly (dimethyl siloxane)—glass device used for singleplex and multiplex cytokine detection. (d) Correlation of AlphaLISA assay signal between customized optics and plate reader.

FIG. 6 demonstrates that a customized optical setup designed herein is capable of measuring the luminescent AlphaLISA assay signal. A customized optical setup, containing a laser diode to excite assay reagents at 680 nm and a CCD or PMT camera for emission signal detection at 615 nm was used. The fiber probe was positioned directly beneath sample for optimum assay signal detection. A poly (dimethyl siloxane)—glass device was used for singleplex and multiplex cytokine detection. The AlphaLISA assay signal was correlated between customized optics and plate reader.

Figure 7:
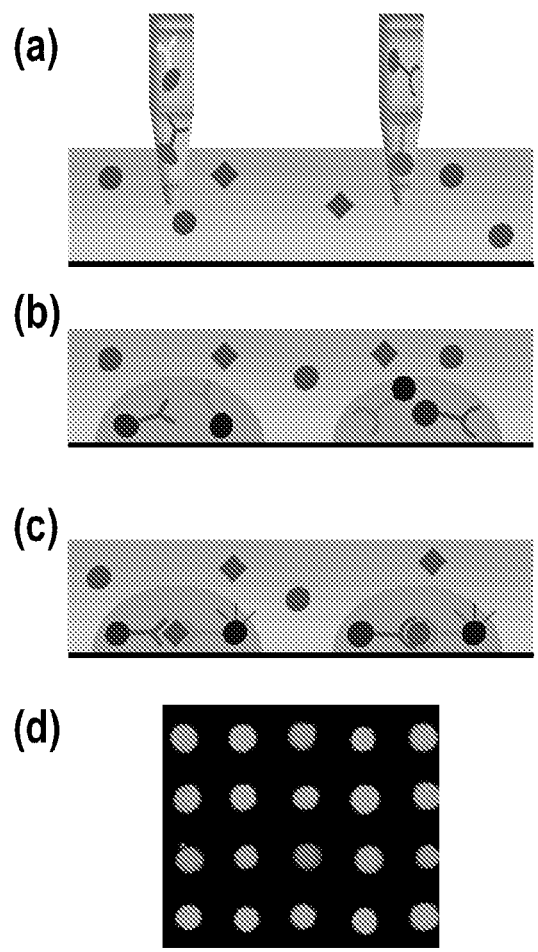
FIG. 7 illustrates solution microarray technology for multiplexed biomarker detection. (a) Antigen samples are mixed with PEG or PVA in a glass cartridge. (b) Arrays of 500 nL DEX assay droplets, containing antibody-conjugated bead-based reagents against specific antigens, are dispensed into the PEG or PVA. (c) Antigen samples diffuse freely from the PEG or PVA phase into the DEX droplets, eliciting a fluorescent signal. A CCD or PMT detects the emitted fluorescence. (d) An array of fluorescent DEX assay droplets on a glass substrate.
Figure 11:
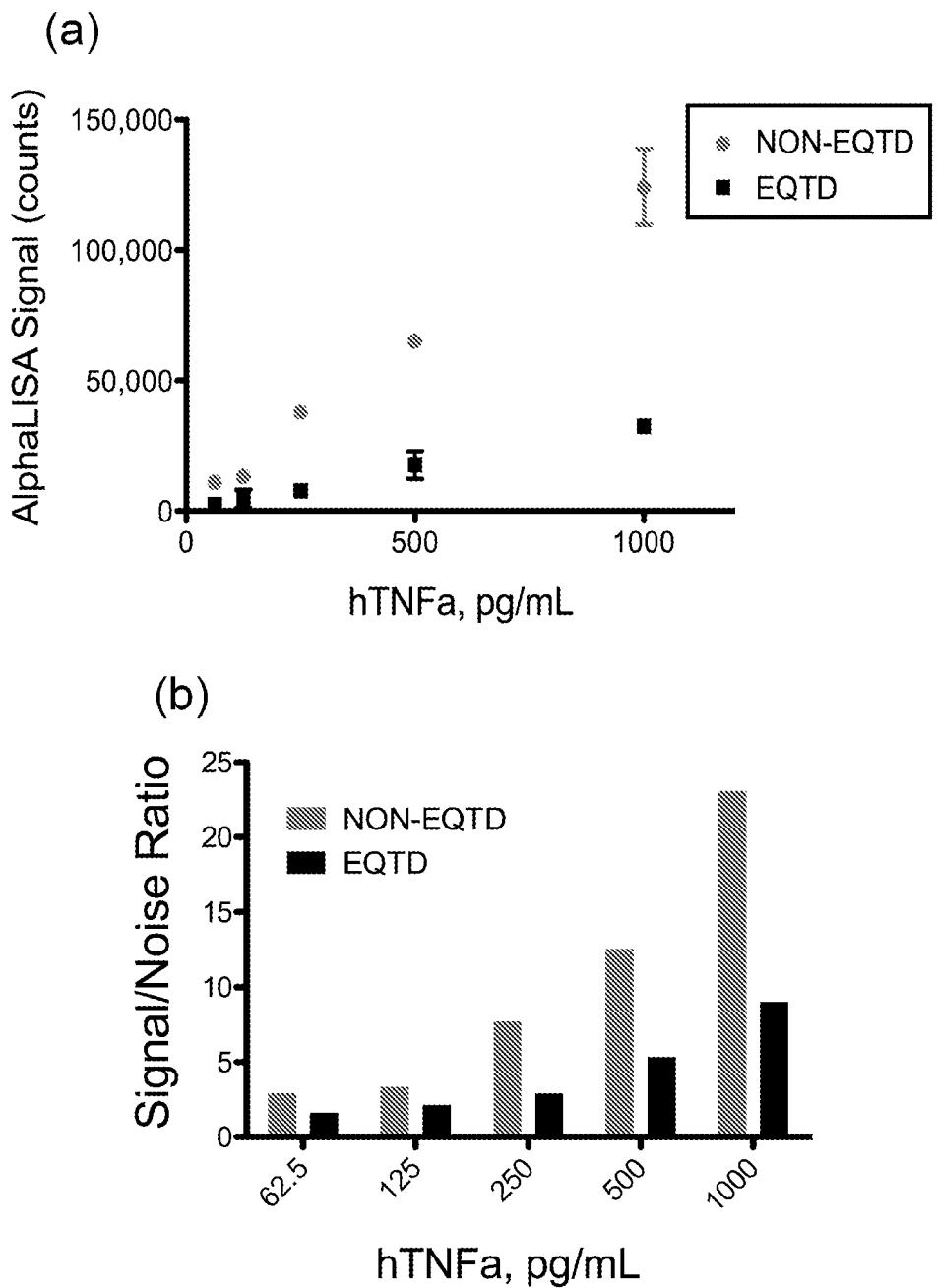
FIG. 11 demonstrates the effect of ATPS preparation on assay signal. (a) 2 uL DEX assays can be performed in either non pre-equilibrated and pre-equilibrated aqueous two-phase systems. (b) 2 uL DEX assays have higher signal-to-noise rations when performed in non pre-equilibrated ATPS versus pre-equilibrated ATPS.

FIG. 11 shows that singleplex biomarker assays can be performed in both pre-equilibrated and non pre-equilibrated aqueous two-phase systems. However, higher signal-to-noise ratios are observed in assays performed using the non pre-equilibrated format. FIG. 7 shows the method utilized when multiplex assays are conducted on glass substrates or glass cartridges. In this method, assay droplets are spatially patterned unto glass substrates, reducing background levels and enhancing signal-to-noise ratio of the assay.

TABLE I

| Sample | Measured Viscosity (cP) |
| --- | --- |
| Brookfield 10 cP Standard Oil; Expected Viscosity, 9.2 cP | 9.15 ± 0.01 |
| 8.0% DEX3.5 | 10.14 ± 0.03 |
| 7.0% DEX10 | 9.84 ± 0.01 |
| 6.0% DEX40 | 10.79 ± 0.07 |
| 3.2% DEX500 | 16.37 ± 0.07 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in electrical engineering, optics, physics, and molecular biology or related fields are intended to be within the scope of the following claims.

We claim:

1. A system, comprising:
   a) a first solution comprising a first polymer and reagents for detecting the presence or absence of an analyte in a test sample, wherein said reagents comprise an antibody that is attached to a particle, and wherein said particle is coated with dextran;
   b) a second solution comprising a second polymer and said test sample, wherein said second solution has a different density than said first solution, and wherein said first and second solutions form an aqueous two-phase system when mixed; and
   c) a solid or semi-solid support.

2. The system of claim 1, wherein said first polymer is selected from the group consisting of polyethylene glycol and dextran.

3. The system of claim 1, wherein said second polymer is selected from the group consisting of polyethylene glycol and dextran.

4. The system of claim 1, wherein said first or second solution comprises two or more polymers.

5. The system of claim 4, wherein said two or more polymers are selected from the group consisting of DEX-methylcellulose, DEX-polyvinyl alcohol, PEG-DEX sulfate, polyvinyl alcohol-DEX sulfate, hydroxypropyldextran-DEX, and DEX sulfate-methylcellulose.

6. The system of claim 1, wherein said analyte is an antigen.

7. The system of claim 6, wherein said reagents further comprise reagents for detecting the presence of binding of said antibody to said antigen.

8. The system of claim 1, wherein said system further comprises a detection component.

9. The system of claim 8, wherein said detection component is selected from the group consisting of a fluorometer, an apparatus for detecting laser induced luminescence and a spectrometer.

10. The system of claim 1, wherein said aqueous two phase system has a viscosity of less than or equal to 10 centipoise (cP).

11. The system of claim 1, wherein said aqueous two phase system has a viscosity of more than or equal to 10 centipoise (cP).

12. The system of claim 1, wherein said first and second solutions are not pre-equilibrated.

13. A method, comprising
   a) contacting a solid or semi-solid support with a first solution comprising a first polymer and reagents for detecting the presence or absence of an analyte in a test sample to form a coated support, wherein said reagents comprise an antibody that is attached to a particle, and wherein said particle is coated with dextran;
   b) contacting a portion of said coated support with a second solution comprising a second polymer and a test sample, wherein said first and second solutions form an aqueous two-phase system when mixed; and
   c) detecting the presence or absence of said analyte in said test sample using said reagents.

14. The method of claim 13, wherein said detecting comprises a method selected from the group consisting of laser induced luminescence, fluorescence resonance energy transfer, fluorescence polarization, transmittance, and color change.

15. The method of claim 13, wherein said test sample diffuses into said first solution and interacts with said reagents.

16. The method of claim 13, wherein said first and second solutions are not pre-equilibrated prior to said detecting step.

* * * * *